United States Patent [19]

Felton et al.

[11] 4,144,331

[45] Mar. 13, 1979

[54] SYNERGISTIC CHLORFENVINPHOS AND PYRETHROID PESTICIDAL COMPOSITION

[75] Inventors: John C. Felton, Sittingbourne; John S. Badmin, Halfway, Minster Isle of Sheppey, both of England

[73] Assignee: Shell Oil Company, Houston, Tex.

[21] Appl. No.: 820,268

[22] Filed: Jul. 29, 1977

[30] Foreign Application Priority Data

Feb. 8, 1977 [GB] United Kingdom ............ 5112/77

[51] Int. Cl.$^2$ .................... A01N 9/36; A01N 9/24; A01N 9/20

[52] U.S. Cl. ................................ 424/219; 424/304; 424/305; 424/308

[58] Field of Search ............ 424/219, 304, 305, 308

[56] References Cited

U.S. PATENT DOCUMENTS

| | | | |
|---|---|---|---|
| 2,956,073 | 10/1960 | Whetstone et al. | 424/207 |
| 3,003,916 | 10/1961 | Gilbert et al. | 424/225 |
| 3,835,176 | 9/1974 | Matsuo et al. | 424/304 |
| 3,987,193 | 10/1976 | Davis et al. | 424/304 |
| 3,996,244 | 12/1976 | Fujimoto et al. | 424/282 |
| 4,024,163 | 5/1977 | Elliott et al. | 260/347.4 |

Primary Examiner—V. D. Turner

[57] ABSTRACT

A pesticidal composition comprising
(a) 2-chloro-1-(2,4-dichlorophenyl)vinyl diethyl phosphate, commonly called chlorofenvinphos, and
(b) at least one pyrethroid compound.

8 Claims, No Drawings

SYNERGISTIC CHLORFENVINPHOS AND PYRETHROID PESTICIDAL COMPOSITION

BACKGROUND OF THE INVENTION

1. Field of the Invention

This invention relates to a pesticidal composition comprising a specific organophosphorus compound and a pyrethroid.

2. Description of the Prior Art

It is well known that certain cyclopropane carboxylic acid derivatives are an important class of pesticides called "pyrethroids". These natural and synthetic pyrethroids have been of considerable interest because of their quick knock-down activity, low persistence as toxic residues and their low mammalian toxicity. Certain derivatives of phenylacetic acids have also been found to have properties of the pyrethroid type. While such compounds are desirable pesticides, because of their relatively complex chemical structures they tend to be difficult or expensive to manufacture.

Applicants have found that certain combinations of synthetic pyrethroids with other known pesticides as hereinafter described possess synergistic activity with respect to dipterous and to ticks, that is to say the activity of the combination of two pesticides produces more than an additive pesticidal effect.

SUMMARY OF THE INVENTION

The present invention provides a pesticidal composition including:

(a) 2-chloro-1-(2,4-dichlorophenyl)vinyl diethyl phosphate (hereinafter referred to as chlorfenvinphos); and (b) at least one pyrethroid insecticide having the formula I

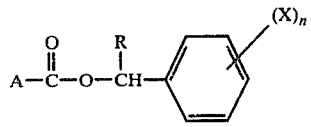

wherein A is an optionally-substituted aralkyl, alkyl or cycloalkyl group, R is hydrogen, cyano or ethynyl, X is alkyl, alkenyl, aralkyl or aryloxy, and n is an integer of from 1 to 5, preferably 1.

Generally speaking, the alkyl, cycloalkyl, and alkenyl groups preferably contain up to 6 carbon atoms and the aralkyl and aryloxy groups contain up to 10 carbon atoms.

It should be noted that optical isomers, cis-trans isomers and other kinds of geometric isomers of the compounds according to formula I are within the scope of the present invention as well as racemates and mixtures of isomers of one or more of the pesticidally active compounds according to formula I. The various isomers of the compounds according to formula I may have different insecticidal toxicities and/or knock down potency. Thus, one may prefer to resolve mixtures of isomers to recover a more pesticidally active isomer or racemic mixture or to prepare the more active forms directly for use in the compositions of the invention.

When A represents an optionally-substituted cycloalkyl group in formula I, the preferred compounds are those containing a cyclopropyl group of formula II

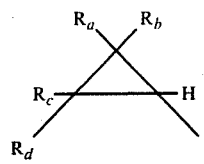

wherein $R_a$ and $R_b$ each represent an alkyl group having from 1 to 6 carbon atoms, especially methyl, or a halogen atom having an atomic number of from 9 to 35, inclusive, especially chlorine atom; or $R_a$ represents a hydrogen atom and $R_b$ represents an alkenyl group having from 2 to 6 carbon atoms, especially an isobutenyl group, optionally substituted by from 1 to 3 chlorine or bromine atoms, especially a mono- or dichlorovinyl group; $R_c$ and $R_d$ each represent an alkyl group having 1 to 6 carbon atoms, or $R_c$ is hydrogen and $R_d$ is an alkylene group having 2 to 6 carbon atoms optionally substituted by from 1 to 3 chlorine or bromine atoms, especially a mono- or dichlorovinyl group; or $R_a$ and $R_b$ together or $R_c$ and $R_d$ together each represent an alkylene group having from 2 to 6, especially 3 carbon atoms.

When A represents an optionally-substituted benzyl group in formula I, preferred compounds are those containing a substituted benzyl group of formula III

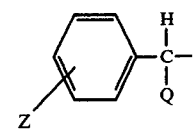

wherein Z represents a halogen atom having an atomic number of from 9 to 35, inclusive, an alkoxy group of 1 to 4 carbon atoms, e.g. methoxy, and Q represents an alkyl group of 1 to 6 carbon atoms, especially a branched chain group such as an isopropyl group.

The pyrethroid compounds (b) are known in art as pesticides as for example when A is a cyclopropyl group of formula II: U.S. Pat. Nos. 3,835,176, 3,987,193, Netherlands publication Nos. 7,307,130, 7,212,973, 7,205,298, Belgian Pat. Nos. 814,819, 820,418, German publication No. 2,407,024 or are disclosed in pending U.S. patent application Ser. No. 771,236, or when A is an optionally substituted benzyl group of formula III: Belgian Pat. No. 801,946; or when A is an alkyl group: Belgian Pat. No. 842,061.

The organo-phosphorous compound (a) is known in the art as a pesticide as for example in U.S. Pat. Nos. 2,956,073, 3,003,916 and 3,116,201.

The most preferred pyrethroids for use in the pesticidal composition according to the invention have the formula I wherein A is alpha-isopropyl-4-chlorobenzyl, 2,2,3,3-tetramethylcyclopropyl, 2-(2,2-dichloro-vinyl)-3,3-dimethylcyclopropyl, or 2-(2,2-dibromovinyl)-3,3-dimethylcyclopropyl; R is hydrogen or cyano; and X is 3-phenoxyphenyl. Especially preferred are the compounds designated Compounds A, B and C in the Examples.

The mixture of chlorfenvinphos and the pyrethroid insecticide not only produces a pesticide having a markedly wider spectrum of activity but also produces surprising synergistic effects especially with respect to dipterous insects e.g. houseflies and sheep blowfly and with respect to ticks, e.g. cattle ticks. Such a mixture therefore has considerable potential in the pesticide market, especially in animal health outlets.

The weight ratio of the pyrethroid insecticide to chlorfenvinphos can be in the range 5:1 to 1:50 but is preferably in the range of from 1:1 to 1:30 or even from 1:5 to 1:25.

The pesticidal composition according to the invention may also employ a carrier, a surface-active agent or both a carrier and a surface-active agent to facilitate application of the composition to the pest or pest-infested environment inhabited by man or animal such as food, plants, pets or livestock at the desired dosage rates. The term "carrier" as used herein means a solid or fluid material, which may be inorganic or organic and of synthetic or natural origin.

Typical solid carriers include natural and synthetic clays and silicates, for example natural silicas, such as diatomaceous earths and aluminium silicates, for example, kaolinites, montmorillonites, and micas. Typical fluid carriers are ketones, for example, methylcyclohexanone, aromatic hydrocarbons, for example, petroleum xylenes and light mineral oils, and chlorinated hydrocarbons, for example carbon tetrachloride. Mixtures of liquids are often suitable. One or more surface-active agents and/or stickers can be included in the formulation. The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol, condensates of these with ethylene oxide and/or propylene oxide; condensation products of fatty alcohols or alkyl phenols, for example p-octylphenol or p-octylcresol, with ethylene oxide and/or propylene oxide; sulphates or sulphonates of these condensation products, alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates, such as sodium dodecylbenzene sulphonate; and polymers of ethylene oxide and copolymers of ethylene oxide and propylene oxide.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The invention also includes a method of combating pests which comprises applying or administering to the pest or pest-infested plant or animal a pesticidally-effective amount of the composition according to the invention.

The invention is further illustrated by the following Examples in which the joint action of two pesticides was analysed according to the method of Yun-Pei Sun and E. R. Johnson, Journal of Economic Entomology, 1960, Volume 53, No. 5, pages 887–892.

Thus, the joint action of two pesticides were analysed by determining the actual toxicity indices of the components and of mixtures of the compounds by reference to dosage-mortality curves. The theoretical toxicity of the mixture is equal to the sum of toxicity indices calculated from the percentage of each component multiplied by its respective toxicity index. Therefore, the joint toxicity Co-toxicity coefficient of a mixture $$= \frac{\text{Actual toxicity index of a mixture}}{\text{Theoretical toxicity index of a mixture}} \times 100$$

A coefficient of a mixture near 100 indicated probability of similar action by the two pesticides; independent action usually should give a coefficient less than 100, while coefficient significantly above 100 strongly indicates synergism.

The compounds tested in the Examples are shown below.

Compound A

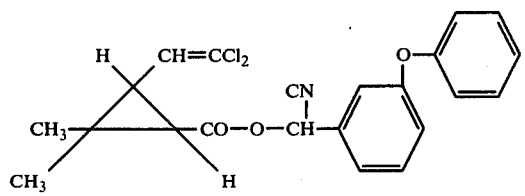

Compound B

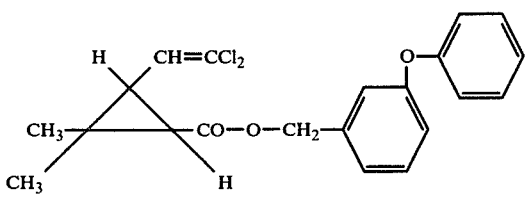

Compound C

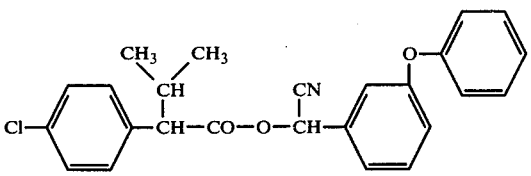

EXAMPLE 1 Activity of Pyrethroid/Chlorfenvinphos mixtures against *Musca Domestica* (housefly)

The coefficient of co-toxicity of a mixture of Compound A with chlorfenvinphos (2-chloro-1-(2,4-dichlorophenyl) vinyl diethyl phosphate) was assessed by the method referred to above.

The $LD_{50}$'s (the lethal dose to kill 50% of the insects) were calculated by employing a series of solutions of Compound A alone and with chlorfenvinphos at varying concentrations. Two to three day old adult female houseflies (*Musca domestica*) were anaesthetised with carbon dioxide, and 1 μl of the test solution was applied by means of a micrometer syringe to the ventral side of the abdomen of each fly, 20 flies being tested. The treated flies were held in glass jars covered with paper tissue held by an elastic band. Cotton-wool pads soaked in dilute sugar solution were placed on top of the tissue as food. After 24 hours the percentage of dead and moribund flies were recorded for each test. From these results the $LD_{50}$'s in micrograms of active material and the coefficient of co-toxicity were calculated and are presented in the following Table I.

TABLE I

| Compound or Compound Mixture | Weight Ratio of Mixture | LD$_{50}$ Musca Domestica | Coefficient of Co-toxicity |
|---|---|---|---|
| Compound A | — | 0.0029 | — |
| Chlorfenvinphos | — | 0.066 | — |
| Compound A/ chlorfenvinphos | 1:10 | 0.017 | 131 |

It will be seen that the coefficient of co-toxicity is clearly in excess of 100 and thereby demonstrate that the two components of the mixture are acting together to produce an effect which is more than an additive, i.e. synergism has been established.

EXAMPLE 2 Activity of Pyrethroid/Chlorfenvinphos mixtures against *Boophilus microplus* (cattle tick)

The coefficients of co-toxicity of mixtures of Compounds A, B and C with chlorfenvinphos (2-chloro-1-(2,4-dichlorophenyl)vinyl diethyl phosphate) were assessed by the method referred to above.

The cattle tick used in this example was an OP-resistant strain, the Mount Alford strain of *Boophilus microplus*. Because it is difficult to assess whether ticks are alive or not, the activity of the compounds and their mixtures were expressed as the percentage reduction in the amount of eggs laid.

The compounds and their mixtures were tested as technical materials dissolved in acetone.

Fully engorged female ticks (*Boophilus microplus*) were placed ventral side uppermost in a petri dish. Each test solution was taken up in a micrometer syringe and a 2 ul droplet of solution applied to the ventral abdomen of each tick. Twelve ticks were treated at each concentration.

Treated ticks were stored (for fourteen days) in an incubator maintained at 27° C. and 80% RH. The reduction in the amount of eggs produced during this period was assessed and the eggs retained for a further period to estimate the percentage hatch.

The ED$_{50}$ of the compounds and their mixtures was assessed by the % reduction in amount of eggs laid.

From these results the ED$_{50}$'s in micrograms of active material and the coefficients of co-toxicity were calculated and are presented in the following Table II.

TABLE II

| Compound or Compound Mixture | Weight Ratio of Mixture | LD$_{50}$ Boophilus microplus | Coefficient of Co-toxicity |
|---|---|---|---|
| Compound A | — | 0.88 | — |
| Chlorfenvinphos | — | 21 | — |
| Compound A/chlorfenvinphos | 1:25 | 4.0 | 278 |
| Compound B | — | 0.70 | — |
| Chlorfenvinphos | — | 21 | — |
| Compound B/chlorfenvinphos | 1:20 | 4.0 | 222 |
| Compound C | — | 4.6 | — |
| Chlorfenvinphos | — | 21 | — |
| Compound C/chlorfenvinphos | 1:5 | 4.8 | 262 |

It will be seen that the coefficients of co-toxicity are all in excess of 100 and clearly demonstrate the synergistic effect of the pyrethroid/chlorfenvinphos mixture.

We claim:

1. An insecticidal or tickicidal composition comprising as the essential active ingredients
    (a) 2-chloro-1-(2,4-dichlorophenyl)vinyl diethyl phosphate; and
    (b) a pesticidally active pyrethroid compound selected from α-cyano-3-phenoxybenzyl 2-(2,2-dichlorovinyl)-3,3-dimethylcyclopropanecarboxylate, 3-phenoxybenzyl 2-(2,2-dichlorovinyl)-3,3-dimethylcyclopropanecarboxylate or α-cyano-3-phenoxybenzyl α-isopropyl-4-chlorophenylacetate in a ratio of (a):(b) of from 1:5 to 50:1.

2. A composition according to claim 1 wherein (b) is α-cyano-3-phenoxybenzyl α-isopropyl-4-chlorophenylacetate.

3. A composition according to claim 1 wherein (b) is α-cyano-3-phenoxybenzyl 2-(2,2-dichlorovinyl)-3,3-dimethylcyclopropanecarboxylate.

4. A composition according to claim 1 wherein (b) is 3-phenoxybenzyl 2-(2,2-dichlorovinyl)-3,3-dimethylcyclopropanecarboxylate.

5. A method of combatting insects or tick pests comprises applying to the pests or a locus an insecticidally or tickicidally effective amount of a composition according to claim 1.

6. A method according to claim 5 wherein (b) is α-cyano-3-phenoxybenzyl α-isopropyl-4-chlorophenylacetate and the ratio of (a):(b) is from 5:1 to 30:1.

7. A method according to claim 5 wherein (b) is α-cyano-3-phenoxybenzyl 2-(2,2-dichlorovinyl)-3,3-dimethylcyclopropanecarboxylate.

8. A method according to claim 5 wherein (b) is 3-phenoxybenzyl 2-(2,2-dichlorovinyl)-3,3-dimethylcyclopropanecarboxylate.

* * * * *